United States Patent [19]

Chan

[11] Patent Number: 4,460,399
[45] Date of Patent: Jul. 17, 1984

[54] DIPHENOXY ETHER FORMAMIDE PLANT-GROWTH REGULATOR

[75] Inventor: David C. K. Chan, Petaluma, Calif.

[73] Assignee: Chevron Research Company, San Francisco, Calif.

[21] Appl. No.: 342,866

[22] Filed: Jan. 26, 1982

[51] Int. Cl.³ .................... A01N 37/18; C07C 103/34
[52] U.S. Cl. ........................................ 71/070; 71/118; 564/219
[58] Field of Search ..................... 71/70, 118; 564/219

[56] References Cited

U.S. PATENT DOCUMENTS

| | | | |
|---|---|---|---|
| 3,032,406 | 5/1962 | D'Amico et al. | 71/70 X |
| 3,447,919 | 6/1969 | Young | 71/70 X |
| 3,798,276 | 3/1974 | Bayer | 564/219 X |
| 4,070,178 | 1/1978 | Johnson et al. | 71/118 X |
| 4,243,410 | 1/1981 | Bohner et al. | 71/118 |
| 4,270,948 | 6/1981 | Takahashi et al. | 71/118 X |
| 4,332,960 | 6/1982 | Trosker et al. | 71/118 X |

*Primary Examiner*—Robert V. Hines
*Attorney, Agent, or Firm*—S. R. LaPaglia; T. G. Dejonghe; L. S. Squires

[57] ABSTRACT

N-(2-[4-(4-trifluoromethylphenoxy)-phenoxy]propyl)-N-methylformamide. The base compound is prepared via formylation of the corresponding amine intermediate. The compounds are useful as fungicides, herbicides and plant-growth regulators and especially as cotton defoliants or desiccants.

3 Claims, No Drawings

DIPHENOXY ETHER FORMAMIDE PLANT-GROWTH REGULATOR

BACKGROUND OF THE INVENTION

This invention relates to N-[4-(substitutedphenoxy)-phenoxyalkylene]-N-alkylformamides and to methods of preparing such compounds and intermediates therefor. The invention also relates to such compounds having plant-growth regulating activity, herbicidal activity, and fungicidal activity.

The term "plant-growth regulating agents" generally refers to compounds which advantageously alter the normal growth pattern of plants. In the case of wheat, the plant-growth agent may alter the growth pattern to produce a shorter stocked plant having more grain. In the case of some plants, plant-growth regulators have been used to cause the plant to defoliate and/or desiccate to facilitate the harvesting of the fruit. In the case of cotton, growth-regulating desiccants and defoliants would be particularly desirable to facilitate picking of the cotton bolls. Such agents must desiccate and/or defoliate without harming the cotton bolls and preferably permit the continued growth of the bolls while acting on the foliage. Desirably, the growth regulator will cause the plant to both desiccate and defoliate, thus greatly facilitating picking.

Growth-regulating compounds typically have some degree of herbicidal activity when used in higher concentration, but the converse is rarely true. A number of halo and trifluoro-phenoxyphenoxy ethers are known to have herbicidal activity. For example, U.S. Pat. No. 4,243,410 discloses α-(4-trifluoromethyl-phenoxyphenoxy)propionic acid alkoxyalkyl amide herbicides. U.S. Pat. No. 4,263,041 discloses N-[5-2-(chloro-4-trifluoromethyl-6-phenoxy)-2-nitro or halo or cyanobenzoyl] carbamates herbicides. A variety of halo and trifluoromethyl diphenyl ether herbicides are also disclosed by U.S. Pat. Nos. 3,475,155; 3,375,157; 4,231,787; 4,263,040; 4,288,243; 4,300,944; European Patent Application No. 0 021 692; German Pat. Nos. DT 2649706 and DT 2450160 (insect-growth regulators); and Belgian Pat. No. 852,701. U.S. Pat. No. 4,294,605 discloses that certain thiadiazole ureas exhibit cotton defoliating activity.

SUMMARY OF THE INVENTION

The plant-growth regulating compound of the present invention can be represented by the following formula:

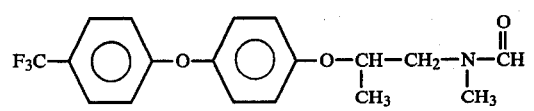

The above compound has an asymmetric carbon atom and hence exists as optical isomers. The respective optical isomers and mixtures thereof are represented by the above formula and are encompassed within the invention.

The above compound of the present invention exhibits preventative fungicidal activity against Grape Downy Mildew and Tomato Late Blight producing fungi and at higher dosages, post-emergent herbicidal activity against a variety of weeds (for example, Mustard, Pigweed, and Lambsquarter). More significantly, the present compound exhibits outstanding cotton desiccating and defoliating activity and does not harm the cotton bolls. The desiccating and defoliating activity is surprising since it was found that even very closely related compounds did not exhibit this activity even though they exhibit herbicidal activity.

The present invention also provides compositions comprising a cotton defoliating or desiccating effective amount of the aforedescribed compound and an agriculturally acceptable carrier. The invention also provides methods for desiccating and defoliating cotton which comprise treating growing cotton plants with a desiccating effective amount of the aforedescribed compounds.

In another embodiment, the invention provides intermediates for the aforementioned compound having the formula:

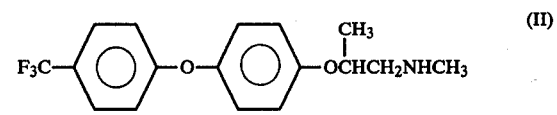

and acid-addition salts thereof. The invention also provides a method for preparing the compound of Formula (I) which comprises treating the compound of Formula (II) with a formylating agent under formylating reactive conditions.

In an another embodiment, the invention provides a method for preparing the intermediate of Formula (II) which comprises the reduction of N-methyl-2-[4-(4-trifluoromethylphenoxy)-phenoxy]-propionamide.

The invention will be further described hereinbelow.

DESCRIPTION OF THE PREFERRED EMBODIMENT

The compounds of the present invention can be prepared by the following process which can be schematically represented by the following overall reaction equation:

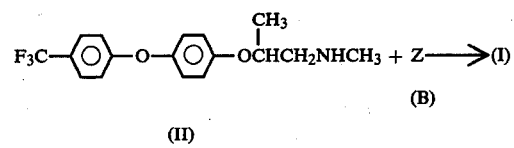

wherein Z is a formylating agent.

This process can be conveniently effected by contacting the compounds of Formula (II) with a suitable formylating agent Z, preferably in an inert organic solvent.

Typically, this process is conducted at temperatures in the range of about from 0° to 150° C., preferably from 25° to 108° C. The reaction is typically conducted as a liquid-phase reaction and reaction pressure is not material except as it effects boiling points. Conveniently, the process is conducted at atmospheric or ambient pressure. Typically, about from 1 to 3 moles of formylating agent is used per mole of Compound (A).

Suitable formylating agents which can be used include, for example, formic anhydride, formic acid, and formyl ester. Suitable formyl esters include those having the formula ROCHO, wherein R is alkyl, or aryl, such as, for example, methyl formate, butyl formate, phenyl formate, and the like. Generally, it is preferable to use formic anhydride.

Formic acid can be used directly or preferably is first converted to the anhydride. This can be conveniently effected in situ by contacting the formic acid with an inert dehydrating agent. Suitable inert dehydrating agents which can be used include, for example, dicyclohexyl carbodiimide, di-p-tolyl carbodiimide, acetic anhydride, 1,1'-carbonyldiimdazole, and compatible combinations thereof. Where formic acid is used directly or formic ester is used, generally higher temperatures, typically about from 78° to 150° C., and higher mole ratios, typically about from 2 to 4 moles of formic acid or formic ester per mole of Compound (II) or higher ratios are preferably used. Whereas when the anhydride is used, lower temperatures, e.g., about 0° to 50° C., and lower mole ratios, about from 1 to 3 moles of anhydride per mole of Compound (II) can be used.

It is also desirable to conduct the process in the presence of an organic amine formylating catalyst to initiate reaction and increase reaction rates. Suitable catalysts which can be used include organic amines such as trimethylene amine, triethylene amine, 4-N,N-dimethylaminopyridine, 4-pyrrolidinopyridine, pyridine, 2,6-dimethylpyridine, and the like and compatible mixtures thereof.

Suitable inert organic solvents which can be used include, for example, methylene chloride, chloroform, benzene, toluene, xylene, and the like and compatible mixtures thereof.

Typically, best results are obtained using formic anhydride as the formylating agent, and conducting the reaction at about from 0° to 25° C. using methylene chloride as the inert organic solvent, and a mole ratio of about from 1 to 1.25 moles of formic anhydride per mole of Compound (II).

Optimum reaction conditions (e.g., temperature, reaction time, mole ratios, solvents, etc.) may vary with the particular formylating agent or organic solvent used but can be determined by routine optimization procedures.

The starting material of Formula (II) can be conveniently prepared by the following process which can be schematically represented by the overall reaction equation:

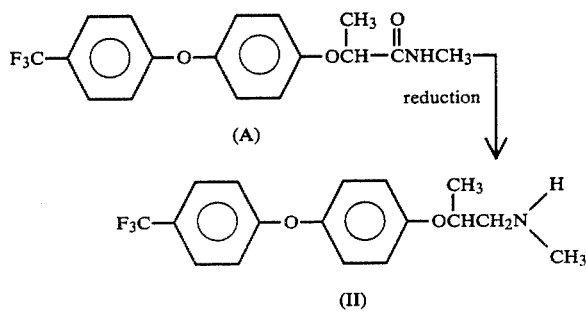

This process can be conveniently effected by contacting the compound of Formula (A) with a reducing agent, preferably in an inert organic solvent. Typically, this process is conducted at temperatures in the range of about from 25° to 150° C., preferably about from 35° to 110° C., for about from 2 to 48 hours, preferably about from 2 to 36 hours. The reaction is typically conducted as a liquid-phase reaction and reaction pressure is largely immaterial except so far as it affects boiling points. Conveniently, the reaction is conducted at ambient or atmospheric pressure.

Suitable reducing agents which can be used include, for example, lithium aluminum hydride, diborane, borane-methyl sulfide, borane-pyridine, and the like and compatible mixtures thereof. Best results are generally obtained using diborane or borane-methyl sulfide. Typically, about from 2 to 3 moles of reducing agent are used per mole of Compound (A).

Suitable inert organic solvents which can be used include, for example, ethyl ether, tetrahydrofuran, benzene, toluene, xylene, and the like and compatible mixtures thereof.

Typically, best results are obtained using borane-methyl sulfide as the reducing agent; tetrahydrofuran as the solvent; reaction temperatures of about 0° to 65° C. for 2 to 8 hours; and mole ratios of about 2 to 3 moles of reducing agent per mole of Compound (A).

Optimum reaction conditions may vary with the particular reducing agent and solvent used and can be determined by routine optimization procedures.

The starting material of Formula (A) can be prepared via the reaction of the corresponding α-substituted propionyl chloride with methyl amine, such as, for example, via the procedure described in Preparation A hereinbelow. The aforementioned α-substituted propionyl chloride is a known compound and can be prepared from via known procedures such as, for example, disclosed by German DOS Nos. 2,223,894 and 2,531,643, and U.S. Pat. No. 4,175,947.

The salts of the compound of Formula (II) can be prepared by reacting the compound of Formula (II) with a mineral or organic acid. Most typically, the salts are encountered as an intermediate when the compound of Formula (II) is reacted with excess formic acid to produce the compound of Formula (I) as described above. This salt could be recovered, but most conveniently, is allowed to convert to the formamide (I) in the reaction mixture.

The compounds of Formulas (I) and (II) and the salts of the Compound (II) can be recovered from their respective reaction product mixtures by any suitable separation and purification procedure, such as, for example, recrystallization and chromatography. Suitable separation and purification procedures are, for example, illustrated in the Examples set forth hereinbelow. Also, if desired, the respective optical isomers can be obtained by conventional resolution procedures, for example, by reacting the isomer mixture with an optically active acid which will yield a mixture of optical salts, of the desired compound, which can be resolved by conventional procedures (e.g., crystallization) into the respective plus and minus optical salts.

It should also be appreciated that where typical preferred process conditions (e.g., reaction temperatures, times, mole ratios of reactants, solvents, etc.) have been given, that other process conditions could also be used, although typically with poor yields or economies.

Definitions

As used herein, the following terms have the following meanings, unless expressly stated to the contrary.

The term "alkyl" refers to both straight- and branched-chain alkyl groups having 1 to 5 carbon atoms. The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "aryl" refers to aryl groups having from 6 through 12 carbon atoms and includes, for example, phenyl, benzyl, naphthyl, phenethyl, naphthylethyl, anthryl, phenanthryl, and the like.

Utility

The compound of Formula (I) and its salts exhibit fungicidal, herbicidal, and most significantly, cotton plant desiccating and defoliating activity.

Typically, where the above compound is used as a cottom desiccant or defoliant, it is applied at a rate of about 0.2 to 10 kilograms, preferably about 0.5 to 5 kilograms per hectare and is applied directly to the foliage of the cotton plant. Also, although in theory the compounds can be applied undiluted, in actual practice they are generally applied as a growth-regulating composition or formulation comprising an effective amount of the compound(s) and an acceptable carrier. An acceptable carrier (agriculturally acceptable carrier) is one which does not significantly adversely affect the growth-regulating effect achieved by the active compounds, save to dilute it, and does not significantly adversely affect the cotton bolls and is generally non-toxic to the environment in the amounts used. Typically, the composition contains about from 0.01 to 5% by weight of the compound of Formula (I). Concentrates can also be made having higher concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils (e.g., paraffin oils) which increase the ultimate desiccating or defoliating effect. For example, it was found that the use of paraffin oils with the present compounds increases the desiccating effect, although somewhat reducing the defoliating effect because of sticking caused by the paraffin oil, thus permitting the use of lower concentration of the growth-regulating compound. The paraffin oil or wax can be conveniently used with the carrier (for example, water) at concentration of about from 0.5 to 5% by weight along with about from 0.01 to 1% by weight, preferably about 0.02 to 0.7% by weight of the present growth-regulating Compound (I). The surface-active agent can be anionic, cationic or non-ionic in character. The composition can also contain various compatible adjuvants, stabilizers, conditioners, insecticides, fungicides, and if desired, other compatible cotton growth-regulating compounds.

At higher concentrations, the compounds of the invention also exhibit post-emergent herbicidal activity against a variety of broad-leaved weeds, including Mustard, Pigweed, and Lambsquarter. The compounds can be applied as herbicides in pure form but more pragmatically are generally applied in a herbicidal composition comprising the active compound in an inert carrier or diluent.

Such herbicidal compositions comprise from about 0.01 to 95% by weight of the herbicidal compound of the invention, intimately admixed with a compatible liquid or solid carrier, e.g., powders, dusts, granules or aerosols. The higher concentration compositions are typically diluted prior to application. The same types of carriers and additives as described above with respect to the growth-regulating composition can also be used for the herbicidal composition.

For post-emergent application, the herbicidal compositions are applied directly to the foliage or other plant parts. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for post-emergent control, the present compounds are applied at rates of about from 0.2 to 60 kg/ha, preferably about from 0.5 to 10 kg/ha.

The compounds of the invention exhibit preventative fungicidal activity against a variety of fungi, including those causing Grape Downy Mildew and Tomato Late Blight. The compounds are preferably applied prophylactically to the foliage and other plant parts of plants which are subject to attack from such fungi, or applied to their environment (soil). The compounds can also be applied to combat fungus in domestic and industrial environments. The optimum dosage will, of course, vary with the particular fungi, host, and environment, but typically will be in the range of about from 100 to 1000 ppm by weight based on the weight of the active ingredient to solvent.

The compounds could be applied in pure form to combat fungi but conveniently and typically are applied as fungicidal formulations comprising the compound(s) of the invention with a biologically inert solid or liquid. Generally, the fungicidal formulation contains the compounds of invention in amounts ranging from 0.005 to 95% by weight and preferably about from 1 to 50% by weight. These formulations are generally concentrates designed for further dilution prior to application.

Typical of the liquid carrier which can be used include liquids such as acetone, water, kerosene, xylene, alcohols, alkylated naphthylene and glycols. Typical solids which can be incorporated with the present compound include the natural clays such as kaolin clays and diatomaceous earth, synthetic fine silica, talc, pyrophyllite, etc.

The fungicidal formulations can also contain stabilizers, spreading agents, sticking agents, fillers, other compatible fungicides and pesticides, and the like.

A further understanding of the invention can be had in the following non-limiting Preparations and Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Also, unless expressly stated to the contrary, geometric isomer and racemic mixtures are used as starting materials and correspondingly, isomer mixtures are obtained as products. Where given, proton-magnetic resonance spectrum (p.m.r. or n.m.r.) were determined at 60 mHz, and signals are assigned as singlets (s), broad singlets (bs), doublets (d), double doublets (dd), triplets (t), double triplets (dt), quartets (q), and multiplets (m).

Preparation A

α-[4-(4-trifluoromethylphenoxy)phenoxy]-N-methyl-propionamide

In this example, 12.4 g (0.104 mole) of thionyl chloride ($SOCl_2$) was added quickly to a stirred slurry containing 30.8 g (0.0944 mole) of α-[4-(4-trifluoromethylphenoxy)-phenoxy] propionic acid and 1 ml of dimethylformamide (catalyst) in 550 ml of methylene chloride. The mixture was refluxed for 1½ hours and then stirred overnight (about 12 hours) at room temperature. A sample was taken and examined by infrared spectrography and showed the absence of —COOH. The mixture was then evaporated under vacuum affording a clear oil which was confirmed by n.m.r. analysis to be α-[4-(4-trifluoromethylphenoxy)-phenoxy]-propionyl chloride.

The clear oil was then dissolved in 100 ml of methylene chloride and added dropwise over a period of ¾ hour to a stirred solution containing 155 g of 40% methylamine (2.0 mole) in 600 ml of dimethoxyethane at −10° C. The reaction mixture was allowed to warm to 16° C. over a period of 3½ hours. Infrared spectrographic examination of a solvent-free sample of this mixture showed complete reaction of the chloride. The mixture was then evaporated under vacuum affording a solid. The solid was then mixed with 350 ml of methylene chloride and the resulting mixture then washed with 150 ml of water. The organic phase was then acidified with 25 ml of aqueous 10% by weight hydrochloric acid. The mixture was then stirred overnight (about 12 hours) at room temperature. The organic phase was then separated, dried over magnesium sulfate and filtered. The filtrate was then evaporated under vacuum affording the title compound as a solid, m.p. 129° to 133° C.

EXAMPLE 1

N-(2-[4-(4-trifluoromethylphenoxy)phenoxy]propyl)-methylamine

In this example, 13.3 g (0.0392 mole) of α-[4-(4-trifluoromethylphenoxy)-phenoxy]-N-methylpropionamide was added portionwise to a stirred slurry containing 1.5 g (0.0392 mole) of lithium aluminum hydride. The resulting mixture was refluxed for 18 hours and then chilled to about 0° C. Then 1.6 ml of water, 1.6 ml of aqueous 15% by weight sodium hydroxide, and 4.8 ml of water were successively added to the chilled mixture and the resulting mixture was stirred until a white precipitate formed. Magnesium sulfate was then added to the mixture to absorb water and then the mixture was filtered. The filter cake was washed thoroughly with ethyl ether. The combined filtrate and ethyl ether washings was evaporated under vacuum affording an oil which crystallized upon standing. Infrared spectrographic examination showed incomplete reduction and accordingly the solid was dissolved in 300 ml of ethyl ether and then 1.5 g of lithium aluminum hydride was added portionwise to this solution. The resulting mixture was refluxed for 18 hours and then chilled to about 0° C. while water (1.5 ml), aqueous (15% by weight), sodium hydroxide (1.5 ml) and water (4.5 ml) were successively added. The mixture was then stirred until a white precipitate separated out. Magnesium sulfate was added and the mixture then filtered and the filter cake washed with methylene chloride. The combined filtrate and washing was evaporated under vacuum affording the title compound as an oil. Complete reduction was confirmed by infrared spectrography and n.m.r. analysis.

EXAMPLE 2

N-(2-[4-(4-trifluoromethylphenoxy)phenoxy]propyl)-N-methylformamide

In this example, 11.7 g (0.2534 mole) of formic acid was added to a stirred slurry containing 26.1 (0.1267 mole) of dicyclohexyl carbodiimide in 300 ml of methylene chloride at about −10° C. A precipitate of dicyclohexyl urea formed. The mixture was then stirred at 0° to 3° C. for 20 minutes and then a solution containing 24.6 g (0.0756 mole) of N-(2-[4-(4-trifluoromethylphenoxy)-phenoxy]propyl)-N-methylformamide and 0.1267 mole of 4-dimethylaminopyridine in 125 ml of methylene chloride was slowly added over a 2-hour period. The mixture was allowed to warm to room temperature and stirred at room temperature overnight (about 12 hours). Thin layer chromatographic analysis of a sample showed complete reaction. The mixture was then filtered and the filter cake washed with methylene chloride. The combined filtrate and washing was washed with 200 ml aqueous 5% by weight hydrochloric acid, then with 200 ml of water and then dried over magnesium sulfate and filtered. The filtrate was evaporated under vacuum affording a semi-oil product. The semi-oil product was treated with ethyl ether and then filtered. The filtrate was evaporated under vacuum affording an oil which was then chromatographed on 300 g of silica gel sequentially eluting with pet (i.e., petroleum ether); 80:20 volume pet:ethyl ether; 60:40 volume pet:ethyl ether; ethyl ether and 96% ethyl ether in methanol affording the title compound as an oil contaminated with water and methanol. The oil was then dissolved in methylene chloride and the resulting solution then washed with water, then with 100 ml of a saturated aqueous solution of sodium bicarbonate and then dried over magnesium sulfate and filtered. The filtrate was evaporated under vacuum affording 10.3 g of the title compound as a clear oil. Elemental analysis: Calculated: C-61.19%, H-5.13%, N-3.96%; Found: C-62.56%, H-5.31%, N-4.05%.

EXAMPLE 3

In this example, the compound of Formula (I), of the invention, and also closely related compounds were respectively tested for cotton defoliating and desiccating activity. The respective tests were conducted as follows:

Spray liquids for each compound were prepared by dissolving 200 mg of the compound to be tested in 5 ml of acetone and then adding 1 ml of a non-ionic surfactant and diluting the solution to 100 ml by the addition of deionized water. This gave spray liquids containing 2000 ppm of the test compound.

Four-to-five week old cotton plants having 4 true leaves above the cotyledonary leaves were used for the tests. The plants were grown under controlled conditions in a greenhouse maintained between 80° F. and 90° F. Within 24 hours before spraying, growth above the second true leaf was removed. Two replicate plants were used for each compound tested.

Each set of replicate plants was sprayed with the spray liquid in a linear spray chamber using a single overhead nozzle. About 1 hour after spraying, the plants were transferred to a greenhouse maintained at 85° F. (±5° F.) where they were allowed to incubate for 13 to 18 days before evaluation. With the exception of the particular compound tested, each test was identically conducted using a test compound spray concentration of 2000 ppm. At this concentration each plant receives a dosage of about 5 mg of test compound. An unsprayed pair of plants were also maintained in the greenhouse and evaluated at the same time as a check.

Defoliation and desiccation was evaluated by observing the 4 true leaves on each plant and counting each leaf as 25% of the total. For example, if only 1 leaf abscises, defoliation would be evaluated as 25%. The combined defoliation/desiccation percentage cannot exceed 100% because a leaf which both abscises and desiccates is noted as defoliation. The evaluations for the 2 test plants were averaged for each compound and are reported as a single combined defoliation-desiccation value in Table A hereinbelow.

TABLE A

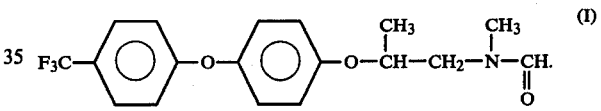

| Compound | | | Percent Combined |
|---|---|---|---|
| No. | X | R | m | Defoliation and Desiccation |
| 1 | H | CH$_3$ | 1 | 100 |
| 2 | H | CH$_3$ | 3 | 0 |
| 3 | Cl | CH$_3$ | 1 | 0 |
| 4 | Cl | H | 1 | 0 |
| Unsprayed Control | | | | 0 |

As can be seen from the above table, Compound 1, of the present invention, exhibited 100% defoliation-desiccation whereas the comparison compounds, even though structurally related to Compound 1, failed to exhibit any observable defoliating or desiccating activity.

The comparison compounds were prepared by following procedures similar to those described in the preparation and examples described above but using the appropriate starting materials.

Obviously, many modifications and variations of the invention, described hereinabove and below in the claims, can be made without departing from the essence and scope thereof.

I claim:

1. A compound having the formula:

$$F_3C-\bigcirc-O-\bigcirc-O-\underset{CH_3}{\underset{|}{CH}}-CH_2-\underset{CH_3}{\underset{|}{N}}-\underset{O}{\overset{\|}{CH}}. \quad (I)$$

2. A cotton plant defoliating-desiccating composition which comprises an amount of the compound of claim 1 effective to desiccate cotton plants and an agriculturally compatible carrier.

3. A method for defoliating and desiccating cotton plants which comprises applying to the foliage of said plants an amount of the compound of claim 1 effective to defoliate and desiccate said cotton plants.

* * * * *